(12) United States Patent
Roetzer et al.

(10) Patent No.: US 8,070,490 B1
(45) Date of Patent: Dec. 6, 2011

(54) TEETH SEPARATING APPARATUS

(75) Inventors: Patrick L. Roetzer, San Ramon, CA (US); Craig Bruns, San Ramon, CA (US)

(73) Assignee: Danville Materials, Inc, San Ramon, CA (US)

( * ) Notice: Subject to any disclaimer, the term of this patent is extended or adjusted under 35 U.S.C. 154(b) by 0 days.

(21) Appl. No.: 12/799,729

(22) Filed: Apr. 29, 2010

(51) Int. Cl.
*A61C 3/12* (2006.01)
*A61C 5/12* (2006.01)
*A61C 15/00* (2006.01)

(52) U.S. Cl. ............................ 433/149; 433/75; 433/142
(58) Field of Classification Search .................... 433/39, 433/75, 76, 136, 138, 139, 140, 142, 143, 433/148, 149, 166; 24/350, 710.8
See application file for complete search history.

(56) References Cited

U.S. PATENT DOCUMENTS

| | | | |
|---|---|---|---|
| 58,687 A * | 10/1866 | Smith | 402/25 |
| 151,265 A * | 5/1874 | Bancroft | 433/140 |
| 350,150 A | 10/1886 | Parr | |
| 371,669 A * | 10/1887 | Carpenter | 433/138 |
| 388,620 A * | 8/1888 | Booth | 433/39 |
| 421,952 A | 2/1890 | Marshall | |
| 425,067 A | 4/1890 | Farrar | |
| 426,253 A | 4/1890 | Elliott | |
| 427,338 A | 5/1890 | Marshall | |
| 436,603 A | 9/1890 | Ivory et al. | |
| 440,509 A | 11/1890 | Sawhill | |
| 450,825 A | 4/1891 | Ivory | |
| 465,555 A | 12/1891 | Cross et al. | |
| 474,131 A * | 5/1892 | Ivory | 433/139 |
| 487,726 A | 12/1892 | Ellard | |
| 511,619 A | 12/1893 | Ivory | |
| 600,257 A | 3/1898 | Capwell | |
| 669,092 A | 3/1901 | Martin | |
| 681,770 A | 9/1901 | Worsley | |
| 775,083 A * | 11/1904 | Ivory | 433/139 |
| 811,849 A | 2/1906 | Hutchinson | |
| 819,136 A | 5/1906 | Herman | |
| 847,778 A | 3/1907 | Ivory | |
| 862,694 A | 8/1907 | Anderson | |
| 1,048,972 A * | 12/1912 | Ivory | 433/148 |
| 1,138,479 A * | 5/1915 | Hough | 451/539 |
| 1,159,496 A * | 11/1915 | Ivory | 433/139 |
| 1,306,696 A | 6/1919 | Ivory | |
| 1,456,294 A | 5/1923 | Arrowsmith | |
| 1,464,532 A | 8/1923 | Ivory | |
| 1,702,869 A | 2/1929 | Ivory | |
| 1,829,898 A | 11/1931 | Ivory | |
| 2,048,856 A | 7/1936 | Ferrier | |
| 2,288,011 A * | 6/1942 | Mizzy | 433/148 |
| 2,585,089 A * | 2/1952 | Caldwell et al. | 24/559 |
| 2,647,315 A | 8/1953 | Dvorak | |
| 4,177,565 A * | 12/1979 | Heasley | 433/75 |
| 4,526,541 A * | 7/1985 | Hubschmid | 433/165 |

(Continued)

*Primary Examiner* — Todd Manahan
*Assistant Examiner* — Michael R Ballinger
(74) *Attorney, Agent, or Firm* — Theodore J. Bielen, Jr.

(57) ABSTRACT

An apparatus for separating teeth utilizing a base member having a first end portion, a second end portion, and an intermediate portion. A first spring extends outwardly from the first end portion while a second spring extends outwardly from the second portion of the base member. A lingual shield spans the distal portions of the first and second springs extending from the base member. A pair of tines overlap one another, one tine extending from the base member, the other extending from the shield. The first and second springs urge the meeting or overlapping of the first and second tines in the vicinity of gap for meeting place between a pair of teeth.

13 Claims, 3 Drawing Sheets

U.S. PATENT DOCUMENTS

| | | | |
|---|---|---|---|
| 4,661,063 A * | 4/1987 | Levy | 433/139 |
| 4,690,642 A * | 9/1987 | Kyotani | 433/142 |
| 4,718,852 A | 1/1988 | Galler | |
| 4,954,082 A | 9/1990 | Weissman | |
| 6,206,697 B1 * | 3/2001 | Hugo | 433/155 |
| 6,666,683 B2 | 12/2003 | Mungcal | |
| 7,083,412 B1 | 8/2006 | Karapetyan | |
| 2003/0129562 A1 * | 7/2003 | Mungcal | 433/149 |
| 2009/0286200 A1 | 11/2009 | Ho | |

* cited by examiner

TEETH SEPARATING APPARATUS

BACKGROUND OF THE INVENTION

The present invention relates to a novel and useful apparatus for separating a pair of adjacent teeth.

Malocclusions are treated by orthodontists using various mechanical and chemical techniques. Prior to the implementation of such techniques, teeth-size modification must take place to correct crowding of teeth adjacent to one another. In the past, such teeth crowding had been corrected by teeth extractions or moving teeth into unstable or unrealistic positions.

The current procedures for the modeling of teeth is often is referred to as "slenderizing" or inter-proximal reduction of enamel. To achieve this result, the practitioner must first separated adjacent teeth and remove enamel with a mechanical device with a saw or rasp. Unfortunately, such techniques require great precision and damage to the tongue, teeth, and lips must be avoided.

Specifically prior methods require the use of wooden wedges to allow the employment of very thin stainless steel diamond coated abrasive strips. In certain cases, screw based separators are used. Wooden wedges induce pain in patients and often cause gingival papillae bleeding, which can confound later adhesive bonding. Moreover, the abrasive stainless strips possess sharp edges and are prone to fracture, such fracturing has caused lacerations on the lips, gingival papillae, floor of the mouth and tongue, since these areas are unprotected. Screw driven separators may also exert excessive forces on the teeth crowns and roots, resulting in fractures in the enamel and dentine.

In the past, many devices have been proposed to separate teeth. For example U.S. Pat. Nos. 436,603, 450,825 show teeth separators that use a support and a moveable wedge which is advanced by a lead screw.

U.S. Pat. Nos. 427,338, 440,509, 465,555, 511,619, 669,092, 1,306,696, and 1,464,532 describe tooth separators using a pair of wedges which fit in the gap between the teeth and employ a threaded member to exert force on one or more of the wedges.

U.S. Pat. Nos. 487,726, 819,136, 847,778, 862,694, and 1,456,294 employ posing wedges, at least one of which is split and expandable to separate teeth.

U.S. Pat. No. 2,647,315 shows a dental matrix instrument in which a screw is employed to place a band which exerts tension on a clip to allow the practitioner to separate teeth a temporary manner in order to insert a filing.

U.S. Pat. Nos. 350,150, 1,702,869, 1,829,898, and 2,048,856 teach teeth separators in which clamps are extended around adjacent teeth, that are caused to separate by one or more lead screws acting on the clamps.

U.S. Pat. Nos. 681,770 and 811,849 describe the use of flanges which partially fit around teeth that are then separated by the use of threaded members.

U.S. Pat. Nos. 425,067, 426,253, and 600,257 show mechanisms for separating teeth which employ lever arms in conjunction with wedges that are moved by screw mechanisms.

U.S. Pat. Nos. 421,952, 4,718,852, 7,083,412 illustrate dental separators which employ threaded mechanisms and wedges that fit in between teeth in combination with matrices that are used to surround or shield one or more teeth.

U.S. Pat. No. 6,666,683 describes a dental ring for installing an inter-proximal filing that utilizes a wedge in combination with a resilient ring.

United States Patent Publication 2009/0286200 shows a separating ring using a pair of legs which provide separation of the teeth by an interconnecting resilient ring.

An apparatus for separating a pair of adjacent teeth while protecting soft tissue to allow the use of enamel removing equipment would be a notable advance in the dental arts.

SUMMARY OF THE INVENTION

The present invention relates to a novel and useful apparatus for separating a pair of adjacent teeth and an enamel removing apparatus used in conjunction with the separating apparatus.

The apparatus of the present invention utilizes a base member having a first end portion, a second end portion, and an intermediate portion interconnecting the first and second end portions. The base member, as well as the remaining portions of the apparatus of the present invention may be formed of a metallic material having a certain degree of resilience. For example, stainless steel may be employed in this regard.

First and second springs, in the form of resilient bands, extend outwardly from the first and second end portion of the base, respectively. Each spring includes a proximal portion connected to the base member and a distal portion. When separated, the distal portions of the springs exert a force which resists such separation. The important of such force will be discussed hereinafter.

A lingual shield spans and connects to the distal portions of the first and second springs. The lingual shield may be slightly convex outwardly from the apparatus of the present invention to hold the tongue of a patient in place while the apparatus of the present invention is employed to separate teeth.

A first tine extends from the base member, in particular the intermediate portion of the base member. The first tine points toward the lingual shield. A second tine extends from the lingual shield towards the first tine. Following separation, the first and second band springs urge the meeting of the first and second tines, due to the resilience or springiness of first and second bands springs. In certain cases, the first tine may overlap the second tine in this regard. The first tine may also be formed with a crease which guides cutting tools that are used for removing enamel from teeth being separated during the "slenderizing" procedure, which will be discussed in greater detail as the specification continues. Also, the edges of the tines may be orthogonal or curved, concavely or convexly.

In addition, a novel saw is revealed in the present application for use with the apparatus for separating teeth, above described. The saw includes a plate having a first side and second side with a perimetric edge between the first and second sides. An abrasive application, such as diamond particles, may form an abrasive surface on the first side of the plate. The second side of the plate is necessarily void of any abrasive material. The shaft connects to the plate and is reciprocated by the use of known reciprocating dental tools. The shaft of the saw may be easily rotated 180 degrees to allow the abrasive side of the plate to remove the enamel from adjacent teeth, seriatum.

It may be apparent that a novel and useful apparatus for separating a pair of adjacent teeth and an enamel removing saw have been heretofore described.

It is therefore an object of the present invention to provide an apparatus for separating a pair of teeth which is easy to use by a dental practitioner in performing inter-proximal reduction of enamel procedures.

Another object of the present invention is to provide an apparatus for separating a pair of adjacent teeth which is durable and reliable in its use.

A further object of the present invention is to provide an apparatus for separating a pair of teeth which includes protection for the papilla, tongue, and lip of the patient when cutting tools are employed to perform slenderizing procedures.

A further object of the present invention is to provide a tooth separator for a pair of adjacent teeth which is formed in one piece and is easily manufactured and sterilized.

Another object of the present invention is to provide a cutting tool for removing enamel in conjunction with a tooth separator that may be easily and efficiently employed to perform inter-proximal enamel reductions.

The invention possesses other objects and advantages especially as concerns particular characteristics and features thereof which will become apparent as the specification continues.

Figure 1:
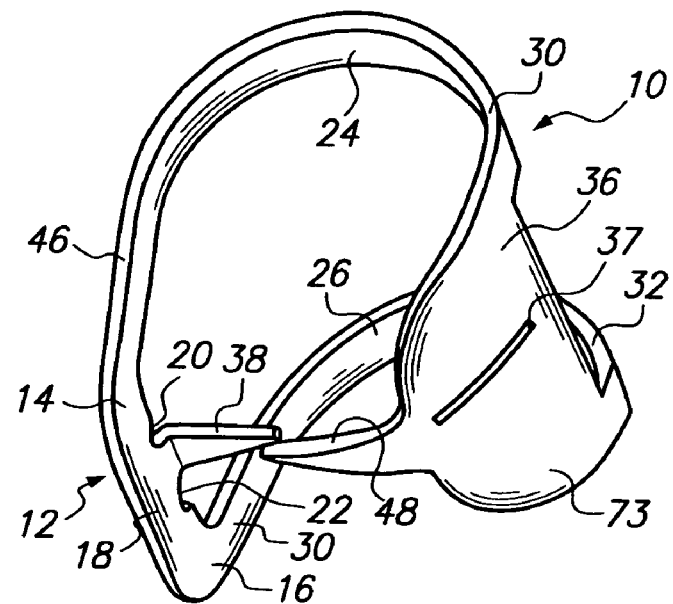
FIG. 1 is a bottom right perspective view of the apparatus of the present invention.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

The tooth separating apparatus of the present invention is depicted in an embodiment 10 depicted in FIGS. 1-3 and 8. Apparatus 10 includes as one of its elements a base member 12. Base member 12 is formed with a first end portion 14, a second end portion 16, and an intermediate portion 18 interconnecting first and second end portions 14 and 16, respectively. Base member 12 also includes notches 20 and 22 which are used to support other dental devices such as a rubber dam forceps or pliers. Base member 12 as well as the remaining portions of apparatus 10, which will be described hereinafter, may be formed of any resilient material such as metal. In particular, 400 series stainless steel suffices in this regard.

First spring 24 and second spring 26 extend from first end portion 14 and second end portion 16 of base member 12, respectively. Springs 24 and 26 may take the form of bands. Springs 24 and 26 include proximal portions 28 and 30, respectively. In addition, springs 24 and 26 possess distal portions 32 and 34, respectively. Any force applied to distal portions 32 and 34 to separate the same from proximal portions 28 and 30 will result in a strong force of resistance tending to move distal portions 32 and 34 toward proximal portions 28 and 30 and into the configuration shown FIGS. 1 and 2.

A lingual shield 36 spans and connects to distal portions 32 and 34 of springs 24 and 26, respectively. Lingual shield 36 possesses a convex side which is intended to face and contact the tongue of the patient when apparatus 10 is employed. A slit 37, FIG. 1, may be positioned on lingual shield 36 to allow cutting or abaiding tools to pass through lingual shield 36.

A first tine 38 extends from base member 12, specifically from intermediate portion 18 thereof. Tine 38 may be triangular in shape, in plan view. In addition, a second tine 40 extends from lingual shield 36. Thus, the urging force tending to position apparatus 10 in the configuration shown in FIGS. 1 and 2, heretofore described, also, tends to force tines 38 and 40 toward one another into the position shown in FIGS. 1 and 2. Tine 38 includes a tip 42 which lies over the tip 44 of tine 40. That is to say, tine 38 overlaps tine 40 in the embodiment of the invention depicted in FIGS. 1 and 2. Tine 38 may simply meet tine 40 such that tips 42 and 44 lie adjacent to one another in another embodiment of the invention. In addition, tines 38 and 40 include upper surfaces 46 and 48 which overly the papilla in the mouth of the patient when apparatus 10 is in use.

Figures 4, 5, 6:
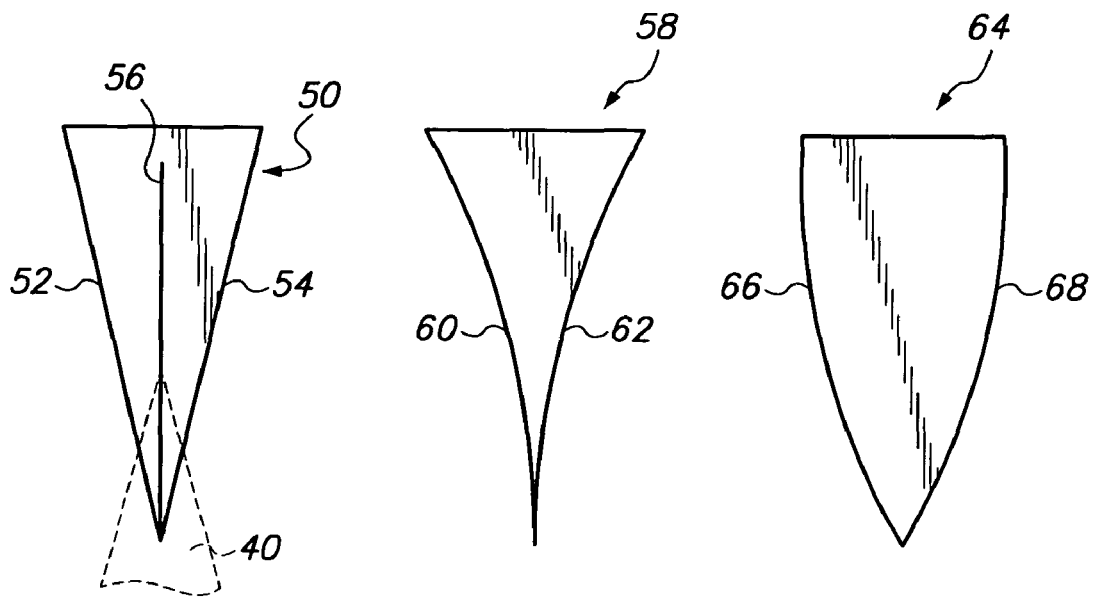
FIG. 4 is a top plan view of a tine extending from the base member with a creased portion.
FIG. 5 is another embodiment of a tine that may be used in the apparatus of the present invention.
FIG. 6 is yet another embodiment of a tine that may be employed in the apparatus of the present invention.

Turning to FIGS. 4-6, it may be observed that tines 38 and 40 may take various configurations. For example, tine 50 includes orthogonal or straight edges 52 and 54. In addition, a crease 56 passes through the central portion thereof, to serve as a guide for enamel cutting tools which may be employed with apparatus 10. FIG. 5 depicts tine 58 which includes concave curved edges 60 and 62. FIG. 6, depicts tine 64 which include convex curved edges 66 and 68. Tines 50, 58, 64 may be applied to an interstice between any adjacent teeth found in the mouth of a patient when device 10 is employed. A plurality of protuberances 69 and 71 are found on side 73 of lingual shield 36 to anchor a cotton roll 75 directly over orifices of the sublingual gland. Likewise, a plurality of protuberances 77 extend from base member to garner an absorbent mass 79 such as cotton, adjacent the lip.

Figure 2:
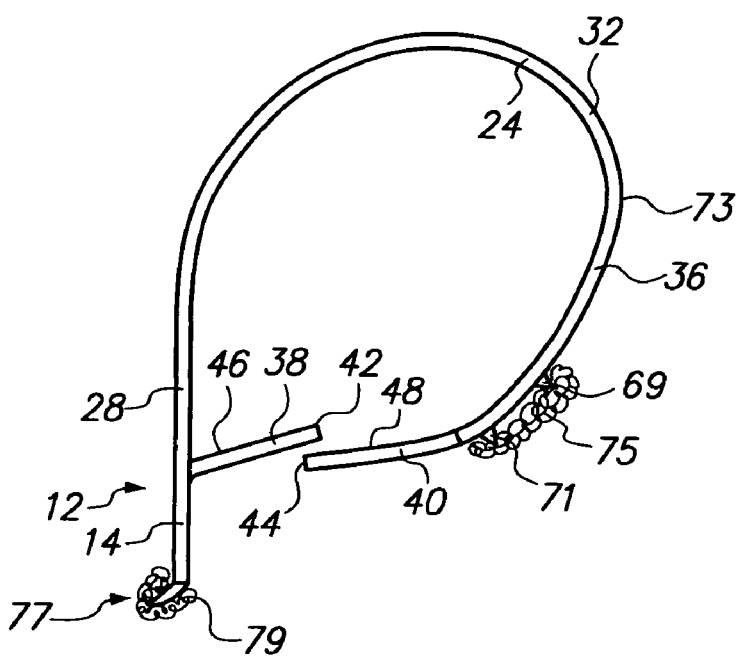
FIG. 2 is a side elevational view of the apparatus of the present invention.
Figure 3:
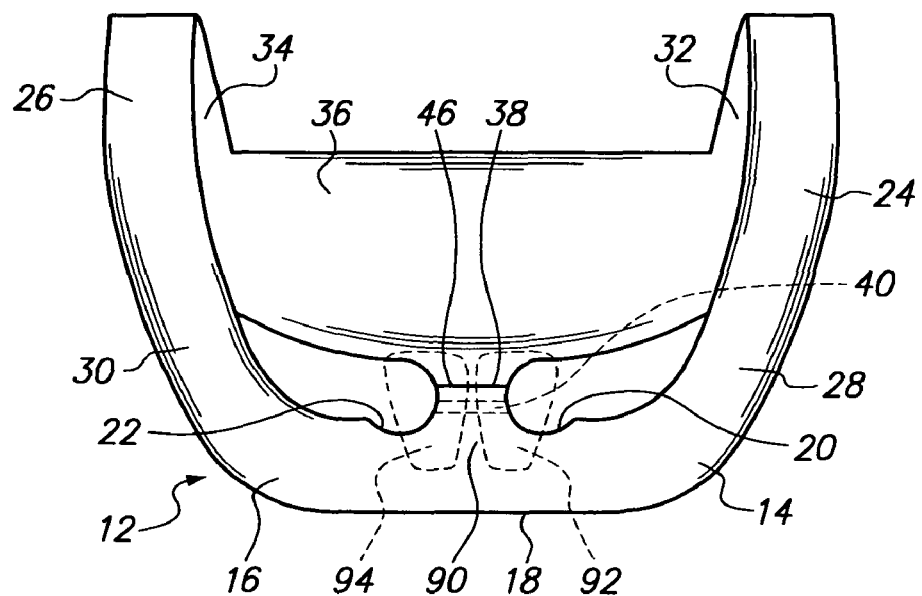
FIG. 3 is a front elevational view of the apparatus of the present invention with a pair of teeth being separated shown in phantom.
Figure 7:
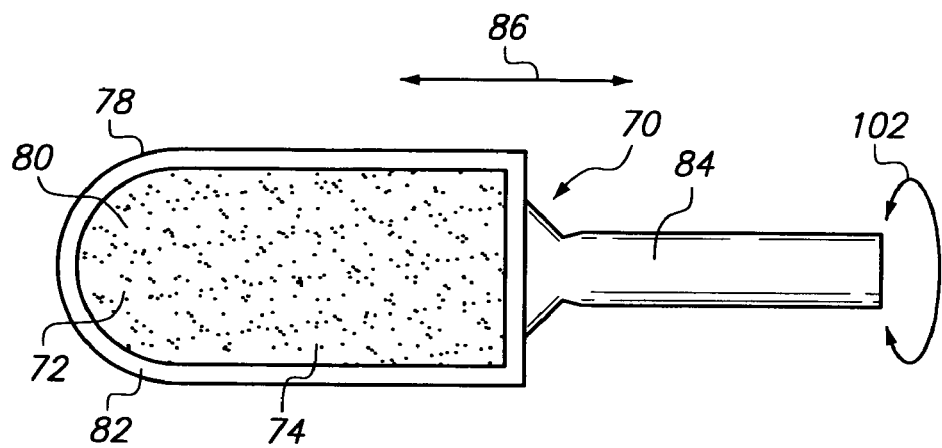
FIG. 7 is a side elevational view of the novel saw which may be employed with the tooth separating apparatus of the present invention.

With reference to FIG. 7, a saw 70 is illustrated which may be used with apparatus 10 shown on FIGS. 1-3. Saw 70 is formed with a thin plate 72 having a first side 74 and an opposite side 76 depicted in FIG. 8. Plate 72 also includes perimeter or edge 78 which separates first side 74 from second side 76. First side 74 plate 72 is formed with a coating or application 80 that may be in a form of diamond particulate matter. Application 80 is found only on first side 74 of plate 72. That is to say, second side 76 of plate 72 does not include an abrasive application. A border region 82 may be formed on first side 74 which is also free of any abrasive application. In this manner, saw 80 is easily used to enter any interstice between adjacent teeth in the mouth of the user, abinitio. A shaft 84 connects to plate 72 and may be employed with any reciprocating dental tool that imparts motion indicated by directional arrow 86. For example, the reciprocating dental tool shown in U.S. Pat. No. 4,954,082 would suffice in this regard and the information provided in this reference is incorporated as a whole into the present application.

Figure 8:
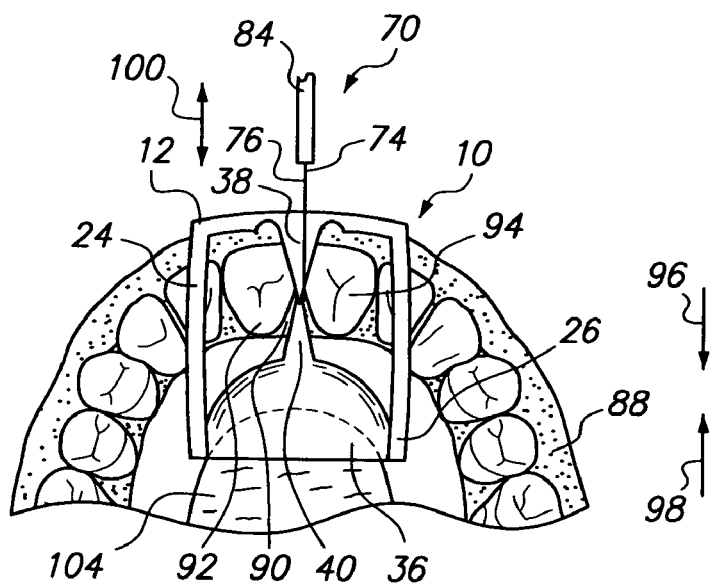
FIG. 8 is a top plan view of a partial arch showing the tooth separating device of the present invention in place between a pair of teeth and the saw of FIG. 7, being used in conjunction therewith.

In operation, apparatus 10 is placed along dental arch 88 of a patient, FIG. 8, such that tine 38 extends towards tine 40 under the force of springs 24 and 26. The distal portions 32 and 38 of springs 24 and 26, respectively have been separated from proximal portions 28 and 30 thereof prior to such placement. Placement of tines 38 and 40 at the interstice 90 between teeth 92 and 94 forces tine 38 toward tine 40 in an overlapping manner, directional arrows 96 and 98, FIG. 8. This force exerted by springs 24 and 26 tends to separate teeth 92 and 94. Protuberances 69, 71 and 77 hold absorbents masses 75 and 79, respectively to staunch glandular generated saliva. At this point, saw 70 may be employed wherein shaft 84 is placed in a reciprocating dental tool and is moved according to directional arrow 100. Abrasive 80 on first side 74 of plate 72 of saw 70 is depicted as having removed enamel from tooth 94. To remove enamel from tooth 92, saw 70 is simple rotated 180 degrees according to directional arrow 102, FIG. 7, in the collette of the reciprocating tool heretofore described. Thus, abrasive application 80 is now available on first side 74 of plate 72 for contact with tooth 92. Slit 37 through lingual shield 36 permits the use of other abrasive tools such as thin abrasive strips, used in the prior art. Following enamel removal, the orthodontist or other dental practitioner may then correct malocclusions by conventional orthodontist techniques. It should be noted that the upper surface of intermediate portion 18 of base member 12, upper surface 46 of tine 38, and the upper surface 48 of tine 40 protect the papilla, as well as the lip of the patient during the use of saw 70. Needless to say, lingual shield 36 protects tongue 104 from any contact with plate 72 of saw 70.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An apparatus for separating a pair of adjacent teeth, comprising:
   a. a base member, said base member including a first end portion, a second end portion and an intermediate portion interconnecting said first and second end portions;
   b. a first spring extending outwardly from said first end portion of said base member, said first spring including a proximal portion connected to base member, and a distal portion;
   c. a second spring extending outwardly from said second end portion of base member said second spring including a proximal portion connected to said base member and a distal portion;
   d. a lingual shield said lingual shield spanning said distal portions of said first and second springs;
   e. a first tine extending from said base member;
   f. a second tine extending from said lingual shield toward said first tine, said first and second springs urging the meeting of said first and second tines; and
   g. a slit positioned in the lingual shield and aligned with the first and second tines for allowing a cutting or abrading tool to pass through the lingual shield.

2. The apparatus of claim 1 in which said first and second tines each include a tip and said base member includes a bottom edge, said tip of said first tine position at a level above base bottom edge of said base member further than said tip of said second member.

3. The apparatus of claim 1 in which said first and second springs comprise bands.

4. The apparatus of claim 1 in which said first tine includes an orthogonal edge.

5. The apparatus of claim 4 in which said second tine includes an orthogonal edge.

6. The apparatus of claim 1 in which said first tine includes a curved edge.

7. The apparatus of claim 6 in which said second tine includes a curved edge.

8. The apparatus of claim 1 which further comprises a saw, said saw passing through the slit and over said first and second tines.

9. The apparatus of claim 8, wherein the saw is for interproximal reduction of enamel and for use with a reciprocating element, the saw comprising:
   a. a plate, said plate having a first side, a second side, and a perimetric edge between said first and second sides;
   b. an abrasive, said abrasive applied to only said first side of said plate; and
   c. a shaft, said shaft connected to said plate and the reciprocating element.

10. The saw of claim 9 which further comprises an abrasive-free zone on said first side of said plate and adjacent said perimeter of said plate.

11. The apparatus of claim 1 in which said first tine includes a crease, and further comprises a saw passing over said first and second tines, said crease of said first tine guiding movement of said saw.

12. The apparatus of claim 1 which additionally comprises a protuberance extending from said lingual shield.

13. The apparatus of claim 1 which additionally comprises a protuberance extending from said base member.

* * * * *